US011320296B2

(12) United States Patent
Connell et al.

(10) Patent No.: US 11,320,296 B2
(45) Date of Patent: May 3, 2022

(54) TEST CAGE FOR TESTING A GAP IN A VEHICLE

(71) Applicant: The Boeing Company, Chicago, IL (US)

(72) Inventors: William John Connell, Woodinville, WA (US); Marcus Karel Richardson, Everett, WA (US)

(73) Assignee: THE BOEING COMPANY, Chicago, IL (US)

( * ) Notice: Subject to any disclaimer, the term of this patent is extended or adjusted under 35 U.S.C. 154(b) by 225 days.

(21) Appl. No.: 16/834,203

(22) Filed: Mar. 30, 2020

(65) Prior Publication Data

US 2021/0302216 A1  Sep. 30, 2021

(51) Int. Cl.
*G01F 17/00* (2006.01)
*G01N 33/00* (2006.01)

(52) U.S. Cl.
CPC ......... *G01F 17/00* (2013.01); *G01N 33/0036* (2013.01)

(58) Field of Classification Search
CPC ............................ G01F 17/00; G01N 33/0036
See application file for complete search history.

(56) References Cited

U.S. PATENT DOCUMENTS

| | | | |
|---|---|---|---|
| 2,937,036 A | 5/1960 | Watkins | |
| 3,867,244 A | 2/1975 | Adams | |
| 3,994,055 A | 11/1976 | Maloney, Jr. et al. | |
| 4,235,398 A | 11/1980 | Johnson | |
| 4,258,510 A | 3/1981 | Guiana | |
| 4,641,464 A | 2/1987 | Andersson et al. | |
| 5,067,291 A | 11/1991 | Evensen | |
| 5,094,040 A | 3/1992 | Bunka | |
| 5,195,281 A | 3/1993 | Kosko | |

(Continued)

FOREIGN PATENT DOCUMENTS

| | | |
|---|---|---|
| CA | 2348501 A1 | 5/2000 |
| DE | 19849696 A1 | 5/2000 |

(Continued)

OTHER PUBLICATIONS

Huber et al., "Controlling Nuisance Moisture in Commercial Airplanes"; Aero 05 (QTR_01-1999); Retrieved from the internet at the following URL: http://www.boeing.com/commercial/aeromagazine/aero_05/textonly/m01txt.html [retrieved on Oct. 30, 2017]; pp. 1-12.

(Continued)

*Primary Examiner* — Jamel E Williams
(74) *Attorney, Agent, or Firm* — Coats & Bennett, PLLC (57) ABSTRACT

A test cage and method for testing a gap formed between a wall and an insulation layer in a vehicle. The test cage includes first and second end walls and a sidewall to form an interior space. Openings extend through one or more of the first and second end walls and the sidewall. The openings are configured to allow air flow through the interior space. Two or more ports extend through the first end wall and are in communication with the interior space. Each of the ports comprises an inner end at the interior space with the inner ends spaced apart within the interior space and also spaced away from the second end wall. Hoses can be connected to the ports to provide for inputting a gas and/or testing the air within the gap.

20 Claims, 8 Drawing Sheets

(56) References Cited

U.S. PATENT DOCUMENTS

| | | |
|---|---|---|
| 5,386,952 A | 2/1995 | Nordström et al. |
| 5,520,009 A | 5/1996 | Jepsen et al. |
| 5,577,688 A | 11/1996 | Sloan |
| 5,752,347 A | 5/1998 | Osborn |
| 5,788,184 A | 8/1998 | Eddy |
| 5,827,598 A | 10/1998 | Larsen et al. |
| 6,212,837 B1 | 4/2001 | Davis et al. |
| 6,315,849 B1 | 11/2001 | Ross |
| 6,491,254 B1 | 12/2002 | Walkinshaw et al. |
| 6,531,206 B2 | 3/2003 | Johnston et al. |
| 6,668,491 B1 | 12/2003 | Bonerb |
| 6,694,686 B2 | 2/2004 | Ready et al. |
| 6,746,567 B2 | 6/2004 | Johnston et al. |
| 6,803,090 B2 | 10/2004 | Castiglione et al. |
| 7,005,175 B2 | 2/2006 | Hachenberg et al. |
| 7,159,620 B2 | 1/2007 | Kissell |
| 7,677,500 B2 | 3/2010 | Redecker |
| 8,157,209 B2 | 4/2012 | Dittmar et al. |
| 8,262,023 B2 * | 9/2012 | Kofinger ............ B64C 1/066 244/119 |
| 8,308,103 B2 | 11/2012 | Boock et al. |
| 8,317,353 B1 | 11/2012 | Martin |
| 8,327,976 B2 | 12/2012 | Müller et al. |
| 2001/0054902 A1 * | 12/2001 | Smith ............ G01R 31/1272 324/544 |
| 2003/0024185 A1 | 2/2003 | Menzies |
| 2003/0102076 A1 | 6/2003 | Johnston et al. |
| 2003/0104170 A1 | 6/2003 | Johnston et al. |
| 2004/0256520 A1 | 12/2004 | Guard et al. |
| 2006/0016204 A1 | 1/2006 | Brokaw et al. |
| 2006/0162262 A1 | 7/2006 | Smith |
| 2010/0044512 A1 | 2/2010 | Paul |
| 2011/0203191 A1 | 8/2011 | Argentina |
| 2012/0040599 A1 | 2/2012 | Hesselbach et al. |
| 2012/0119024 A1 | 5/2012 | Redecker |
| 2012/0126059 A1 * | 5/2012 | Piuzzi ............ B64C 1/403 244/119 |
| 2012/0234979 A1 | 9/2012 | Smith |
| 2013/0009010 A1 | 1/2013 | Auriac et al. |
| 2013/0020434 A1 | 1/2013 | Müller et al. |
| 2013/0168496 A1 | 7/2013 | Roth |
| 2013/0344762 A1 | 12/2013 | Vermont et al. |
| 2016/0160509 A1 | 6/2016 | Anic |
| 2016/0194879 A1 | 7/2016 | Gleason |
| 2017/0106965 A1 | 4/2017 | Dickson et al. |
| 2017/0305027 A1 | 10/2017 | Broeker |
| 2017/0370643 A1 | 12/2017 | Gray et al. |
| 2018/0065726 A1 | 3/2018 | Berryessa |
| 2019/0106191 A1 | 4/2019 | Hitchcock et al. |
| 2019/0127039 A1 | 5/2019 | Hitchcock et al. |

FOREIGN PATENT DOCUMENTS

| | | |
|---|---|---|
| DE | 10154063 A1 | 5/2003 |
| DE | 102006023209 A1 | 11/2007 |
| DE | 102008025389 A1 | 7/2009 |
| DE | 102008037143 A1 | 2/2010 |
| DE | 102006039292 B4 | 7/2010 |
| DE | 102011001267 A1 | 9/2012 |
| EP | 1358064 A2 | 11/2003 |
| WO | 9118237 A1 | 11/1991 |
| WO | 0037313 A1 | 6/2000 |
| WO | 2003097344 A1 | 11/2003 |
| WO | 2008101986 A1 | 8/2008 |

OTHER PUBLICATIONS

ECHO Air Inc, "About ECHO Air Inc", retrieved from the internet: http://www.indoorair.ca/echo/index.php [retrieved on Oct. 4, 2018]; pp. 1-4.

* cited by examiner

FIG. 11

TEST CAGE FOR TESTING A GAP IN A VEHICLE

TECHNOLOGICAL FIELD

The present disclosure generally relates to testing devices and methods and, more particularly, to devices and methods for testing within a gap formed between a wall and an insulation layer within a vehicle.

BACKGROUND

In an aircraft, the outer skin is spaced from the walls and ceiling of a passenger cabin (or other compartment), and the gap is at least partially filled with an insulation layer. The insulation layer functions to moderate the temperatures within the interior of the aircraft. This includes insulating the interior from the cold outer skin that occurs when the aircraft is at high elevations during flight. This also includes insulating the interior from the heated outer skin that occurs when the vehicle is parked or flying at lower altitudes (e.g., during takeoff and descent).

The air in the gap between the outer skin and insulation layer is tested to determine the adequacy of the insulation layer. The testing can include checking the air pressure within the gap and air movement in the gap. The testing includes extending one or more hoses through the insulation layer from the interior space and into the gap. The hoses are then used to perform the testing, such as to input tracer gas into the gap and to be in communication with the gap to determine air pressure and/or air movement.

An issue with current testing methods is how to accurately place the one or more hoses in the gap. The ends of the hoses may need to be spaced away from the outer skin to ensure that airflow into and/or out of the gap is not restricted. When testing for air pressure and concentrations of tracer gas, the ends of the hoses should be located in a central area of the gap. This positioning provides for accurate air pressure measurements because temperature differences of the air against the hot or cold outer skin can influence the readings. For testing concentrations, more accurate readings are obtained from the more well-mixed air in the center of the gap.

SUMMARY

One aspect is directed to a test cage for testing a gap formed between a wall and an insulation layer in a vehicle. The test cage comprises a first end wall, a second end wall, and a sidewall that extends between and spaces apart the first and second end walls. An interior space is formed within the first and second end walls and the sidewall. Openings extend through one or more of the first and second end walls and the sidewall. The openings are configured to allow air flow through the interior space. One or more ports extend through the first end wall and are in communication with the interior space. Each of the ports comprises an inner end at the interior space with the inner ends spaced apart within the interior space and also spaced away from the second end wall.

One aspect is directed to a method of testing a gap in a vehicle that is formed between a wall and an insulation layer. The method comprises inputting a gas through a first hose that extends through the insulation layer and into a test cage that is positioned in the gap. The first hose is connected to a first port located at a first position on the test cage and is spaced away from the wall of the vehicle. The method also comprises testing the air in the gap using a second hose that is connected to a second port that is located at a second position on the test cage that is spaced away from the first port and with the second hose extending through the insulation layer and to the test cage. The second hose is spaced away from the first hose on the test cage and the second hose is spaced away from the wall of the vehicle.

One aspect is directed to a method of testing a gap in a vehicle that is formed between a wall and an insulation layer. The method comprises: attaching a first hose to a first port in a test cage; attaching a second hose to a second port in the test cage with the first and second ports spaced apart on the test cage; positioning the test cage within the gap that is formed between the wall and the insulation layer; extending the hoses through the insulation layer with second ends of the hoses extending outside of the gap; inputting a gas through the first hose and into the gap; and testing the air in the gap through the second hose.

DETAILED DESCRIPTION

Figure 1:
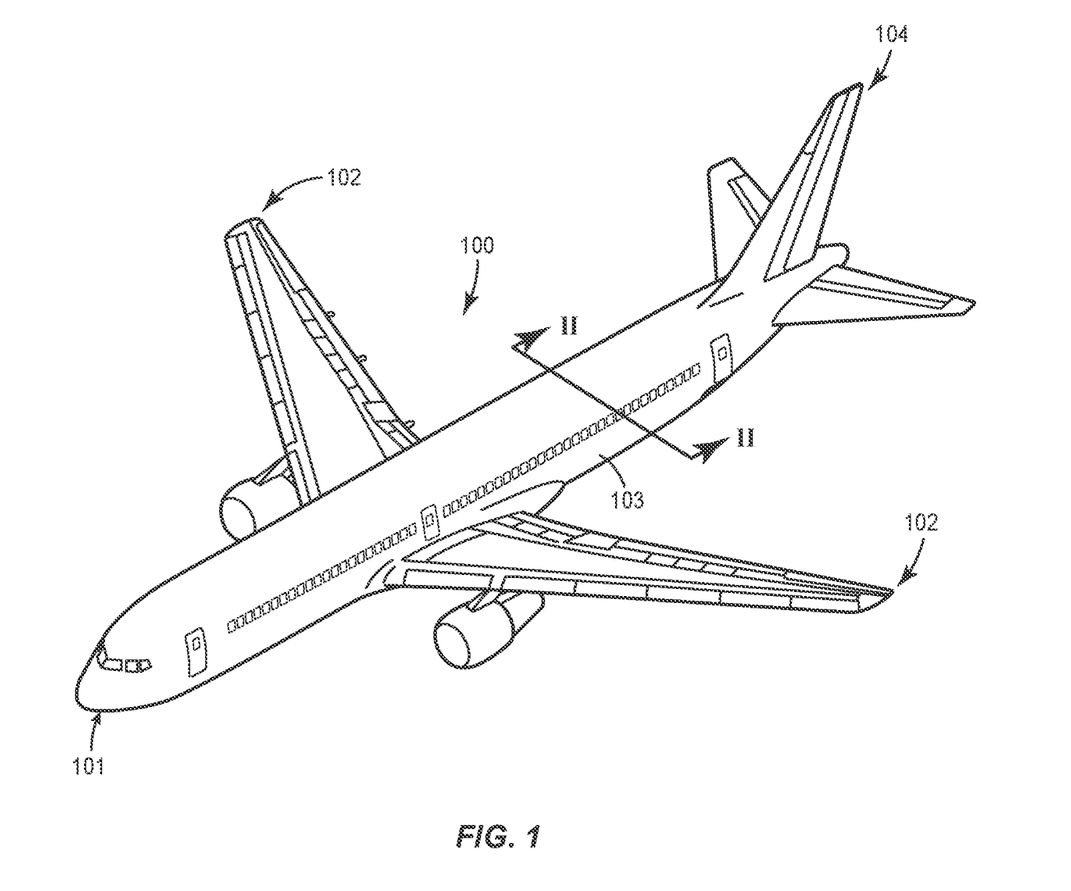
FIG. 1 is a perspective view of a vehicle.
Figure 2:
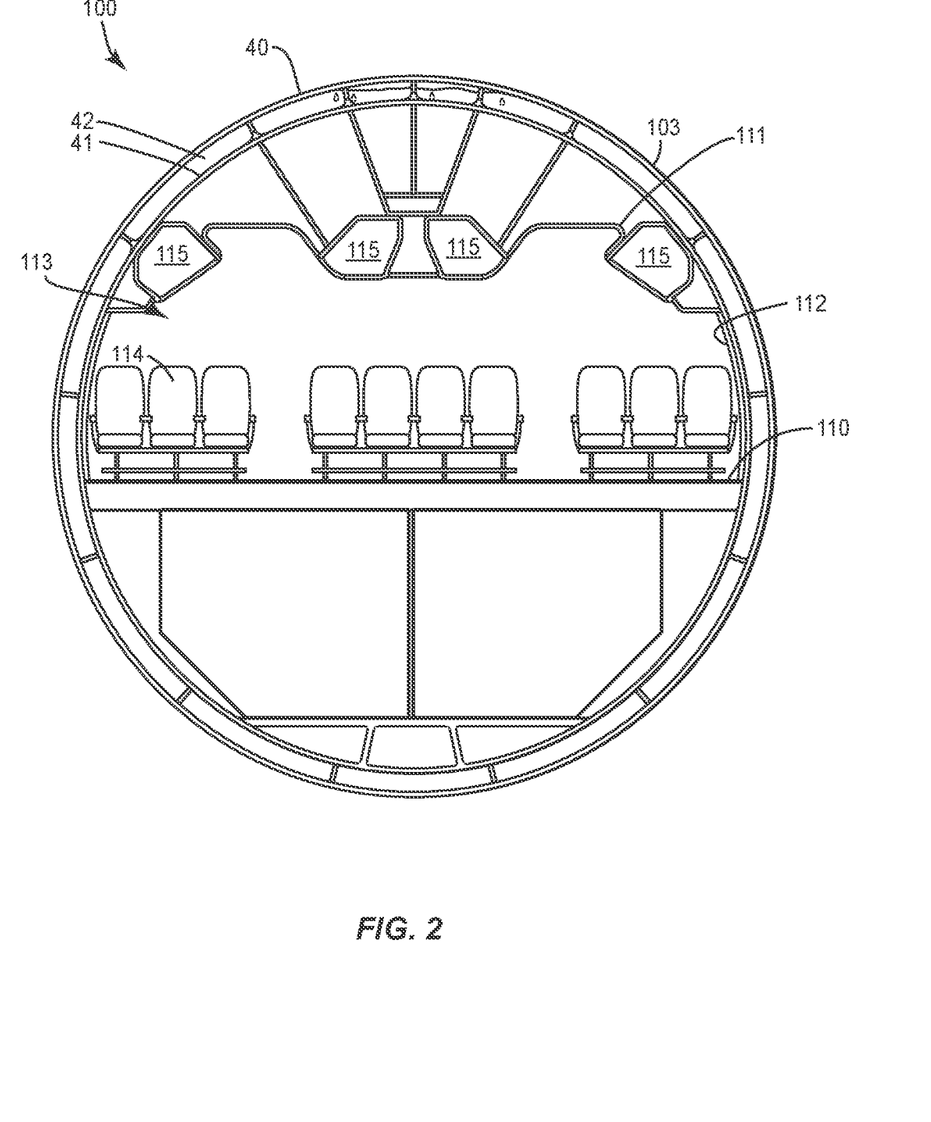
FIG. 2 is a section view of the vehicle of FIG. 1 cut along line II-II.

The testing devices and methods apply to a variety of different vehicles. FIG. 1 illustrates one type of vehicle 100, namely an aircraft 100. The aircraft 100 includes a nose 101, wings 102, a fuselage 103, and a tail 104. FIG. 2 is a cross-sectional, schematic view of the aircraft 100 indicated by view arrows II-II in FIG. 1. FIG. 2 illustrates a simplified version of a portion of the aircraft fuselage 103 that includes an outer wall 40. The fuselage 103 also includes an insulation layer 41 positioned inward towards a center of the fuselage 103 from the outer wall 40. A gap 42 is formed between the outer wall 40 and the insulation layer 41. The fuselage 103 also includes an interior space 113 that includes a cabin with a floor 110, ceiling 111, and aesthetic fascia walls 112. The interior space 113 can be equipped with seats 114 and luggage compartments 115 to accommodate passengers.

During flight, the outer wall 40 is cooled by the outside air at high altitude. When the vehicle 100 is on the ground and at lower elevation, the outer wall 40 is heated by the sun. The air in the gap 42 and the insulation layer 41 insulate the interior space of the vehicle 100 and prevent or limit the transfer of hot or cold temperatures into the interior space of the vehicle 100. The insulation layer 41 also acts as a shield to prevent the water formed from condensation on the outer wall 40 from escaping from the gap 42 and moving into the interior space 113. The insulation layer 41 also prevents or reduces the amount of moisture that moves from the interior space 113 into the gap 42.

Testing is performed in the gap 42 to determine the effectiveness of the insulation layer 41. The testing can detect if the insulation layer 41 is fouled, drooping, or otherwise ineffective. The testing can include different methods, including but not limited to measuring the air pressure within the gap 42 and testing the concentration of a tracer gas to determine air movement.

Figure 3:
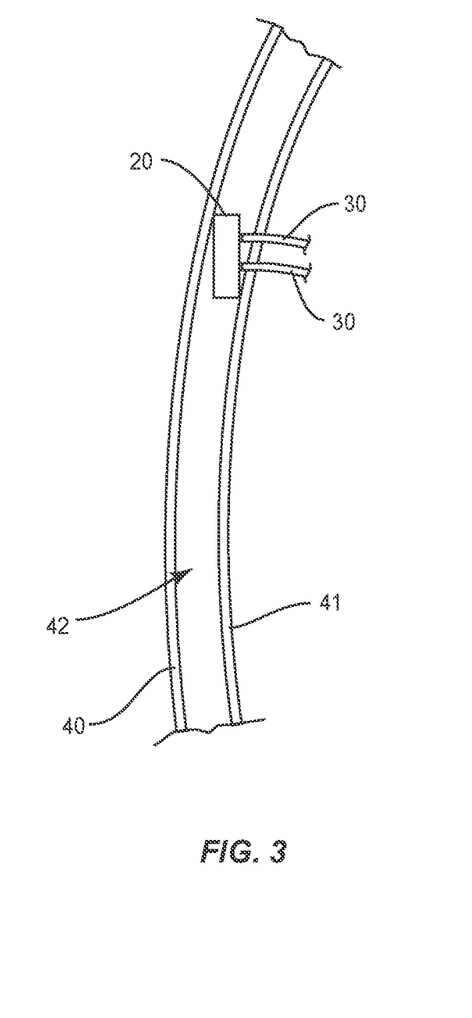
FIG. 3 is a side view of a test cage positioned in a gap formed between an outer wall and insulation layer of a vehicle.

FIG. 3 illustrates a test cage 20 positioned within the gap 42 formed between the outer wall 40 and the insulation layer 41. The test cage 20 is attached to one or more hoses 30 for various steps during the process, such as but not limited to introducing a tracer gas into the gap 42, removing a gas from the gap 42, or providing access to the gap 42 for testing air pressure. The test cage 20 positions the ends of the hoses in the gap 42 and away from the outer wall 40 to provide for accurate testing.

FIGS. 4-7 illustrate a test cage 20 sized to fit within the gap 42. The test cage 20 includes a first end wall 22 and a second end wall 23. A sidewall 21 extends between the first and second end walls 22, 23. The first and second end walls 22, 23 and the sidewall 21 can be single continuous sections, or can be constructed from multiple discrete sections. The test cage 20 can include various shapes and sizes to fit within and/or conform to the gap 42. The example illustrated includes the test cage 20 having a substantially cylindrical shape with each of the first and second end walls 22, 23 being flat and with a circular sectional shape. In one example, the test cage 20 has a diameter D within a range of substantially 1.5 inches-2.0 inches and a height H of substantially 0.5 inches. In other examples, the sectional shape can include but is not limited to polygonal and oval.

The test cage 20 is constructed from a thermally insulating material. This prevents or reduces the test cage 20 from being cooled or heated when placed in contact with the outer wall 40 and potentially causing issues with the testing. Examples of materials include but are not limited to plastics, polymers, fiberglass, and ceramic.

An interior space 24 is formed within the test cage 20 between the first and second end walls 22, 23 and the sidewall 21. Openings 27 extend through one or more of the first and second end walls 22, 23 and the sidewall 21 and allow for gas to flow through the test cage 20. In one example, one or more openings 27 extend through each of the first and second end walls 22, 23 and the sidewall 21 to provide for the circulation of air within the interior space 24 and more accurate testing results than could occur with a more enclosed configuration.

One or more ports 25 extend through first end wall 22 and into the interior space 24. Each port 25 includes an outer end 28 away from the interior space 24 and an inner end 29 at the interior space 24. Each port 25 includes a hollow fitting 26, e.g. a hollow tube, that extends outward from the first end wall 22 away from the interior space 24. The fitting 26 provides for engaging with a hose 30. The fittings 26 include one or more tapered sections to further engage with the hose 30 and prevent inadvertent detachment.

Figure 4:
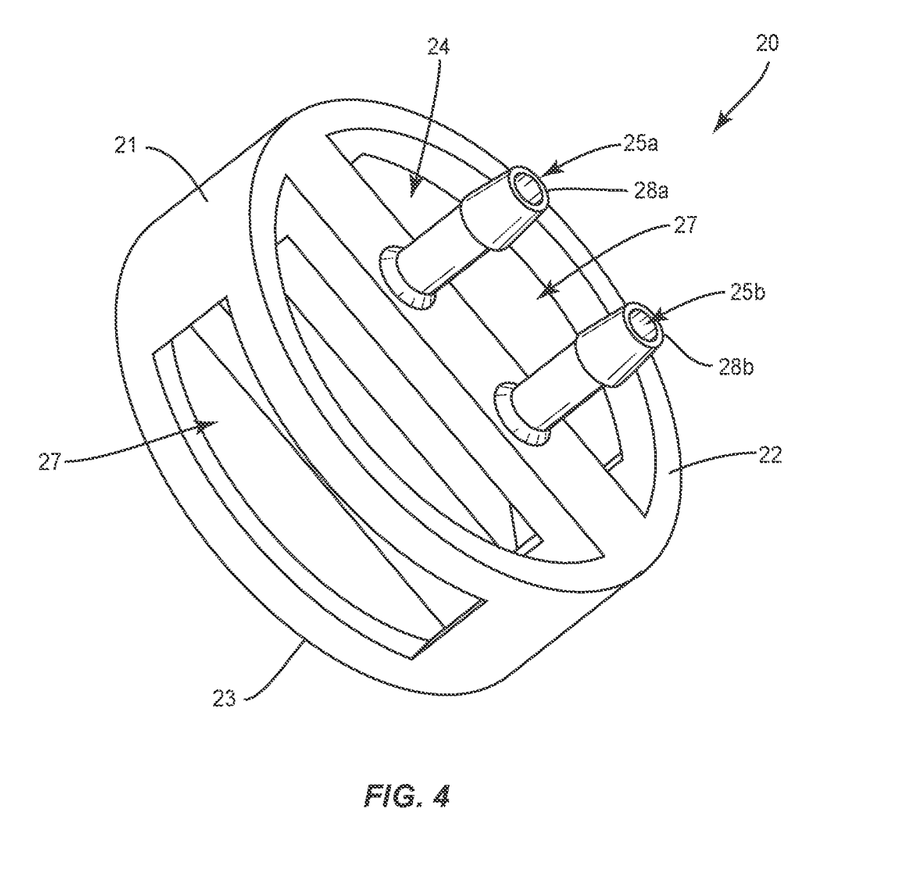
FIG. 4 is a perspective view of a test cage.
Figure 5:
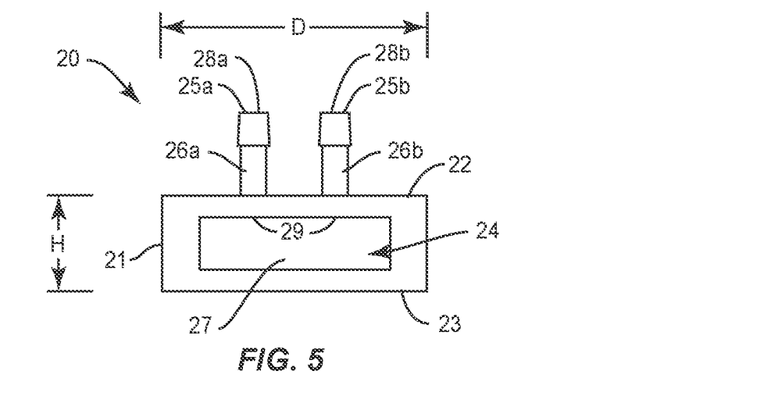
FIG. 5 is a first side view of the test cage of FIG. 4.
Figure 6:
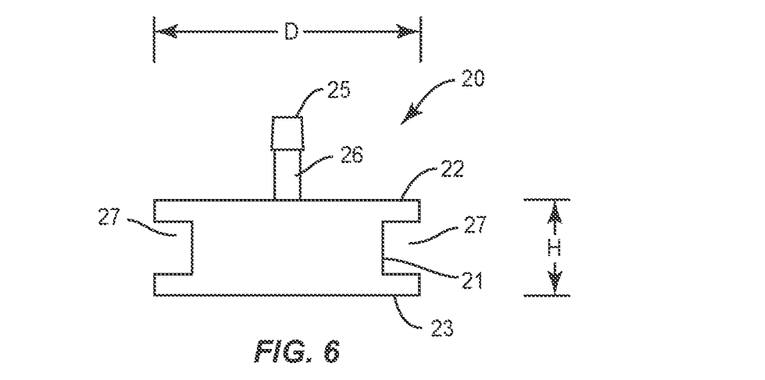
FIG. 6 is a second side view of the test cage of FIG. 4.
Figure 7:
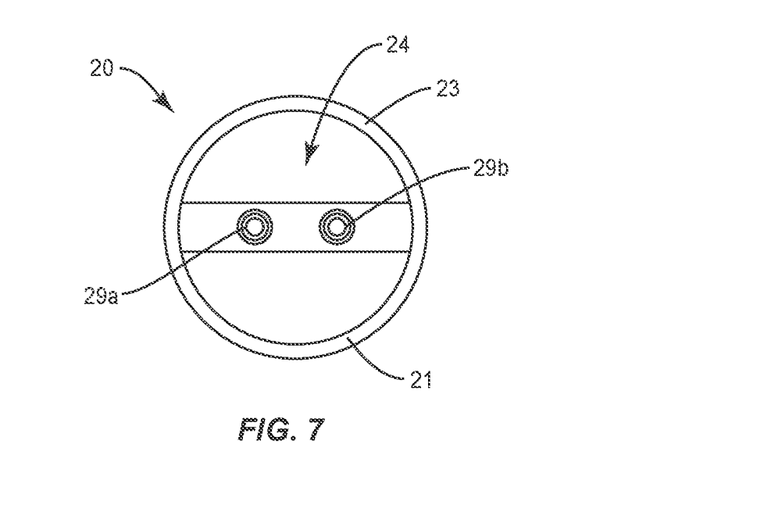
FIG. 7 is a bottom view of a test cage.

The one or more ports 25 accommodate the various testing methods. In one example, one or more ports provide for inputting gas into the gap 42 and testing the air pressure within the gap 42. In one example as illustrated in FIGS. 4-6, the test cage 20 includes a pair of ports 25a, 25b. A first port 25a provides for gas to be inputted into the gap 42. A second port 25b provides for testing the air pressure within the gap 42 and/or testing a concentration of the gas in the gap 42. Another example includes a single port 25 for either inputting gas and/or testing the air pressure and/or gas concentration. Other examples include three or more ports 25 to perform the various testing steps.

Figure 8:
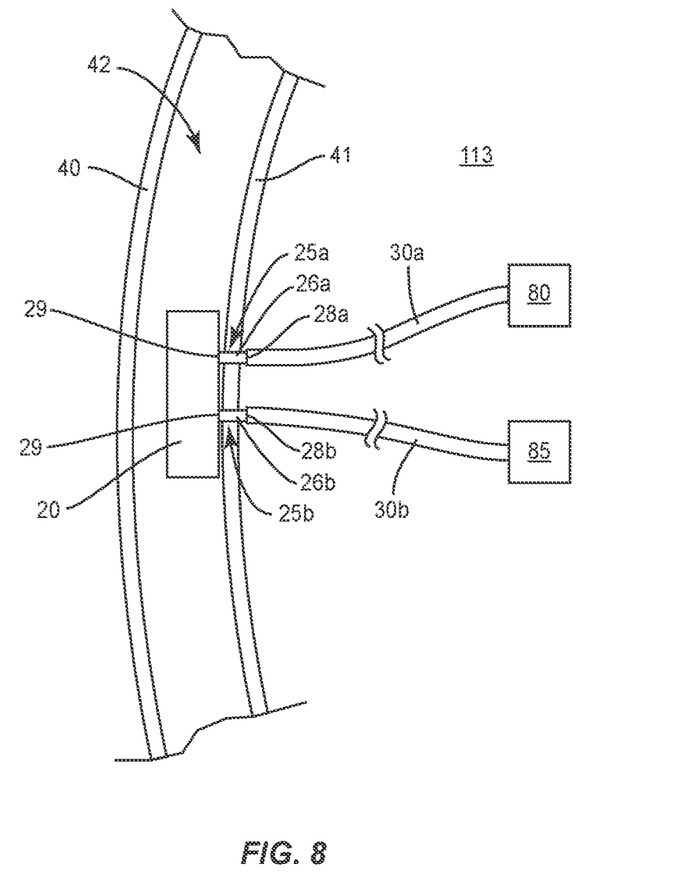
FIG. 8 is a side view of a test cage attached to hoses and positioned in a gap formed between an outer wall and insulation layer of a vehicle.

FIG. 8 illustrates an example of a test cage 20 positioned in a gap 42. The test cage 20 is positioned against the inner side of the insulation layer 41 and is spaced away from the outer wall 40. The inner ends 29 of the ports 25 are positioned at a central section of the gap 42 and are spaced away from the outer wall 40. This positioning provides for accurate air pressure measurements because temperature differences of the air against the hot or cold outer wall 40 can influence the readings. The positioning also facilitates concentration testing because more accurate readings are obtained from the more well mixed air in the center of the gap. In one example as illustrated in FIG. 8, the inner ends 29 face into the gap 42. In one example, the inner ends 29 are positioned at the center of the gap 42.

In one example as illustrated in FIG. 8, the fittings 26a, 26b extend through the insulation layer 41 with the outer ends 28a, 28b of the ports 25a, 25b positioned within the interior space 113 and away from the gap 42. A first hose 30a is attached to the port 25a and to a gas source 80 to input gas into the gap 42. The gas source 80 can include various configurations, such as a pressurized container with a fitting to attach the hose 30a. A second hose 30b is attached to a second one of the ports 25b and to a pressure sensor 85. The pressure sensor 85 is configured to detect the air pressure within the gap 42. In one example, the test cage 20 is positioned in the gap 42 with the inner ends 29 of the ports 25 facing towards the outer wall 40.

One testing method includes inputting a tracer gas, such as xenon or argon, through a first hose 30a and into the gap 42. The second hose 30b includes a concentration sensor 85 that detects the tracer gas. This testing method determines the amount of air movement within the gap 42 based on the concentration of detected and the distance between the inner ends 29 of the test cage 20. In examples with two or more ports 25, the inner ends 29 of the ports 25 are spaced apart along the interior space 24. This spacing prevents gas that is being input into the gap 42 from potentially adversely affecting the testing for the air pressure.

In one example, the test cage 20 includes a single port 25 and the attached hose 30 includes a splitter that can adjust between different configurations that provide for both inputting gas and testing for the gas concentration.

Another testing method includes a pressure sensor 85 attached to a hose 30. In one method, the air pressure within the gap 42 is measured by the pressure sensor 85. In another method, one or more additional hoses 30 are attached to the test cage 20. A gas is inserted into the gap 42 through the one or more hoses 30 prior to or during the pressure sensing.

In the various examples, one or more of the gas source 80 and the sensor 85 can be directly connected to the test cage 20. This can include one or more connected to the fitting 26 and engaged with the outer end 28 of the port 25.

The test cage 20 spaces the hoses 30 away from the outer wall 40 where they could be blocked or otherwise impaired to prevent their functioning. In one example as illustrated in FIG. 8, the test cage 20 is spaced away from the outer wall 40. In another example as illustrated in FIG. 3, the test cage 20 is positioned in contact with the outer wall 40.

In one example, the test cage 20 provides for attaching two or more hoses 30. One or more of the hoses 30 provides for inputting one or more gases into the gap 42. Additional one or more of the hoses 30 provide for testing the pressure within the gap 42. In one example, the pressure testing occurs at the same time gas is being inputted into the gap 42. In another example, the pressure testing occurs at times when no gases are being input into the gap 42. This separating timing prevents the inputted gas from potentially interfering with the pressure testing.

Figure 9:
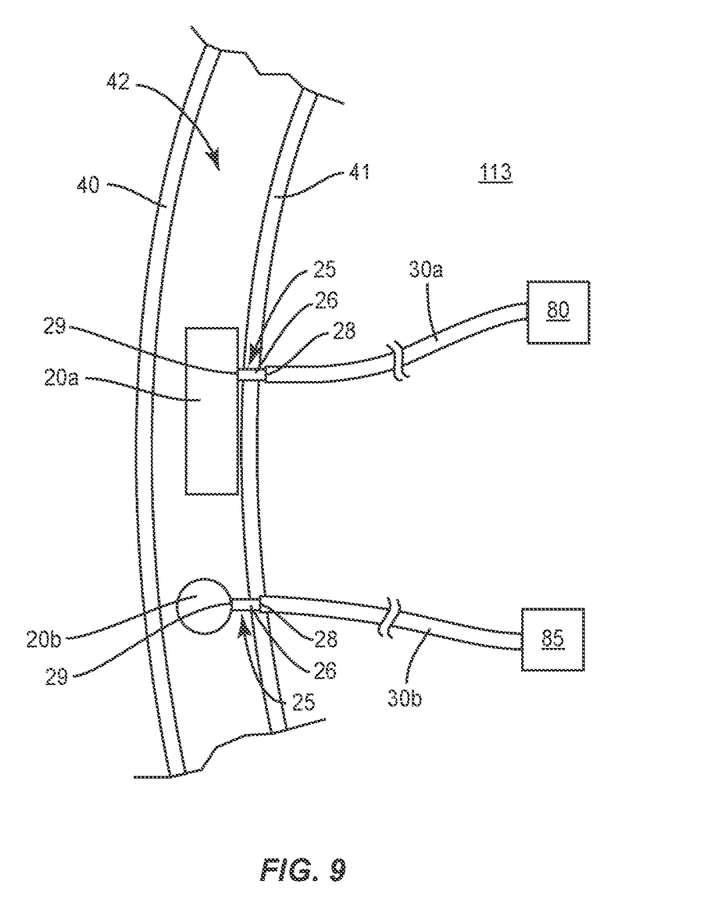
FIG. 9 is a side view of test cages attached to hoses and positioned in a gap formed between an outer wall and insulation layer of a vehicle.

FIG. 9 illustrates an example with a pair of test cages 20a, 20b spaced apart and positioned in the gap 42. The first test cage 20a is connected with a first hose 30a to a gas source 80 to input a tracer gas into the gap 42. The second test cage 20b is spaced apart from the first test cage 20a. The second test cage 20b is connected with a second hose 30b to a sensor 85 to detect the tracer gas in the gap 42. The amount of tracer gas detected by the sensor 85 indicates the amount of airflow within the gap 42 and thus the effectiveness of the insulation layer 41. In one example, a large amount of airflow indicates that air is entering into and escaping from the gap 42 through the insulation layer 41 and/or openings in and around the insulation layer 41. A relatively small amount of airflow indicates that the insulation layer 41 is performing at a higher efficiency by preventing the air to enter and escape from the gap 42.

In examples with multiple test cages 20, the spacing between the test cages 20 can vary. In one example, the test cages 20 are spaced apart at different vertical positions within the gap 42. In another example, the test cages 20 are spaced apart at different horizontal positions (e.g., at different locations along the cabin of the interior space 113). Other examples can include a combination of both.

The test cage 20 can be inserted into the gap 42 at different times during the construction of the vehicle 100. In one example, the test cage 20 is inserted prior to installation of the insulation layer 41. The test cage 20 is positioned in proximity to the outer wall 40. The insulation layer 41 is then installed over the outer wall 40 thus positioning the test cage 20 in the gap 42. In another example, the test cage 20 is installed in the gap 42 after the insulation layer 41 has been installed. This can occur when a test cage 20 is installed into an existing vehicle 100. A hole is cut into the insulation layer 41 and the test cage 20 is inserted through the hole and into gap 42. The insulation layer 41 is then positioned back over the hole and over the test cage 42.

Figure 10:
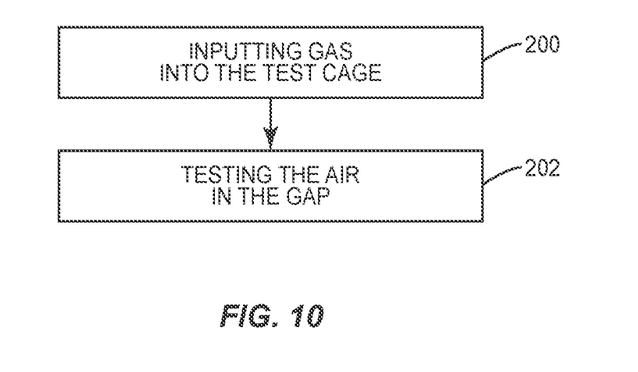
FIG. 10 is a flowchart diagram of a method of testing a gap in a vehicle that is formed between a wall and an insulation layer.

FIG. 10 illustrates a method of testing air pressure within the gap 42. The method includes inputting a gas through a first hose 30a that extends through the insulation layer 41 and into a test cage 20 positioned in the gap 42 (block 200). The first hose 30a is connected to a first port 25a located at a first position on the test cage 20 that is spaced away from the wall 40 of the vehicle 100.

The method includes testing the air in the gap 42 (block 202). The testing uses a second hose 30b that is connected to a second port 25b located at a second position on the test cage 20 that is spaced away from the first port 25. The second hose 30b extends through the insulation layer 41 and to the test cage 20. The second hose 30b is spaced away from the first hose 30a on the test cage 20 and spaced away from the wall 40 of the vehicle 100.

Figure 11:
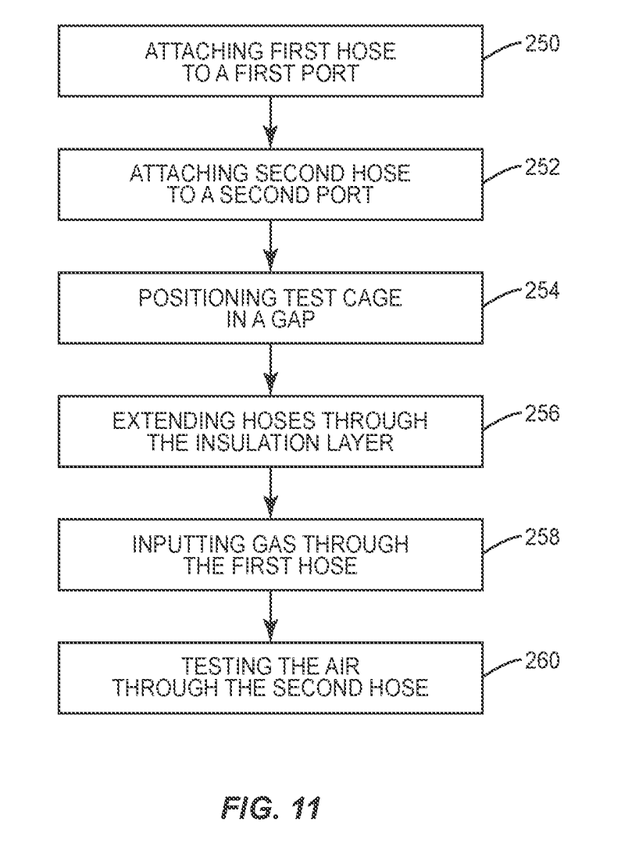
FIG. 11 is a flowchart diagram of a method of testing a gap in a vehicle that is formed between a wall and an insulation layer.

FIG. 11 illustrates a method of testing air within a gap 42. The method includes attaching a first hose 30a to a first port 25a in a test cage 20 (block 250). A second hose 30b is attached to a second port 25b in the test cage 20 (block 252). The first and second ports 25a, 25b are spaced apart on the test cage 20. The test cage 20 is positioned within the gap 42 that is formed between the wall 40 and the insulation layer 41 (block 254). The hoses 30a, 30b extend through the insulation layer 41 (block 256). The second ends of the hoses 30a, 30b extend outside of the gap 42.

The testing includes inputting a gas through the first hose 30a and into the gap 42 (block 258). The method includes testing the air in the gap 42 through the second hose 30b (block 260).

In one example, a single test cage 20 is used when just a single pressure measurement is taken. In another example, a single test cage 20 is used to determine the concentration of a tracer gas that was injected at one location to determine the amount of airflow at that location. In one example, the test cage 20 is used to test the insulation layer 41. In one example, a test cage 20 with a single port 25 is used with a pressure sensor 85 to monitor the air pressure in the gap 42.

In one example, two or more different test cages 20 are used when a tracer gas is injected at a first location and samples from the one or more additional locations are tested to determine the direction of air flow within the space 42. In another example with multiple test cages 20, pressure differences at the different test cages 20. In one example, tracer gas is injected through a first test cage 20. The tracer gas is tested for in one or more downstream test cages 20. The amount of tracer gas detected at the one or more downstream locations provides an indication of the insulation layer. In one example, if the one or more downstream test cages 20 do not detect a positive measure of tracer gas or an amount that is less than an expected amount, this indicates that the insulation layer 41 is compromised.

The examples described above include the test cage 20 positioned within a gap 42 formed between an outer wall 40 and an insulation layer 41. The test cage 20 can also be used in other gaps 42 between different members. One example includes a gap formed between interior walls or members within a vehicle.

The device 10 can be used on a variety of vehicles 100. Vehicles 100 include but are not limited to manned aircraft, unmanned aircraft, manned spacecraft, unmanned spacecraft, manned rotorcraft, unmanned rotorcraft, satellites, rockets, missiles, manned terrestrial vehicles, unmanned terrestrial vehicles, manned surface water borne vehicles, unmanned surface water borne vehicles, manned sub-surface water borne vehicles, unmanned sub-surface water borne vehicles, and combinations thereof.

By the term "substantially" with reference to amounts or measurement values, it is meant that the recited characteristic, parameter, or value need not be achieved exactly. Rather, deviations or variations, including, for example, tolerances, measurement error, measurement accuracy limitations, and other factors known to those skilled in the art, may occur in amounts that do not preclude the effect that the characteristic was intended to provide.

The present disclosure can be carried out in other ways than those specifically set forth herein without departing from essential characteristics of the disclosure. The present aspects are to be considered in all respects as illustrative and not restrictive, and all changes coming within the meaning and equivalency range of the appended claims are intended to be embraced therein.

What is claimed is:

1. A test cage for testing a gap formed between a wall and an insulation layer in a vehicle, the test cage comprising:
   a first end wall;
   a second end wall;
   a sidewall that extends between and spaces apart the first and second end walls;

an interior space formed within the first and second end walls and the sidewall;

openings that extend through one or more of the first and second end walls and the sidewall, the openings configured to allow air flow through the interior space;

one or more ports that extend through the first end wall and are in communication with the interior space, each of the ports comprising an inner end at the interior space, the inner ends spaced apart within the interior space and also spaced away from the second end wall.

2. The test cage of claim 1, further comprising a plurality of hoses connected to the ports in the first end wall, with one of the hoses connected to each one of the ports.

3. The test cage of claim 2, wherein a first one of the hoses is connected to a gas source to move a gas into the interior space and a second one of the hoses is connected to a sensor to detect the air within the interior space.

4. The test cage of claim 1, wherein at least one of the openings extends through the first end wall, at least one of the openings extends through the second end wall, and at least one of the openings extends through the sidewall.

5. The test cage of claim 1, wherein the test cage is constructed from a thermally insulating material.

6. A method of testing a gap in a vehicle that is formed between a wall and an insulation layer, the method comprising:

inputting a gas through a first hose that extends through the insulation layer and into a test cage that is positioned in the gap with the first hose connected to a first port located at a first position on the test cage and that is spaced away from the wall of the vehicle; and testing air in the gap using a second hose that is connected to a second port that is located at a second position on the test cage that is spaced away from the first port and with the second hose extending through the insulation layer and to the test cage with the second hose spaced away from the first hose on the test cage and the second hose being spaced away from the wall of the vehicle.

7. The method of claim 6, further comprising contacting the test cage against the wall of the vehicle while spacing the first and second hoses away from the wall of the vehicle.

8. The method of claim 6, further comprising inputting the gas through the first hose and into an interior space of the test cage that is formed between first and second end walls.

9. The method of claim 6, wherein testing the air in the gap using the second hose comprises attaching a pressure sensor to the second hose at a point that is outside of the gap and within an interior of the vehicle and sensing air pressure within the gap.

10. The method of claim 6, wherein testing the air in the gap using the second hose comprises attaching a concentration sensor to the second hose and sensing a concentration of the gas in the gap.

11. The method of claim 6, further comprising positioning inner ends of the first and second ports in the test cage towards the wall of the vehicle, with one of the first and second hoses connected to each one of the first and second ports.

12. The method of claim 6, further comprising positioning openings in the test cage away from the insulation layer and the wall to provide for air flow through an interior space of the test cage.

13. A method of testing a gap in a vehicle that is formed between a wall and an insulation layer, the method comprising:

attaching a first hose to a first port in a test cage;

attaching a second hose to a second port in the test cage, the first and second ports being spaced apart on the test cage;

positioning the test cage within the gap that is formed between the wall and the insulation layer;

extending the hoses through the insulation layer with second ends of the hoses extending outside of the gap;

inputting a gas through the first hose and into the gap; and testing air in the gap through the second hose.

14. The method of claim 13, further comprising spacing the hoses in the gap and away from the wall of the vehicle.

15. The method of claim 14, further comprising inserting fittings that extend outward from the test cage through the insulation layer and attaching the hoses to the fittings outward from the gap.

16. The method of claim 13, further comprising testing air pressure of the gap through the second hose while inputting the gas into the gap through the first hose.

17. The method of claim 13, further comprising positioning the test cage in the gap and spacing the test cage away from the wall of the vehicle.

18. The method of claim 13, further comprising inserting the gas into an interior space of the test cage.

19. The method of claim 13, further comprising positioning the test cage in proximity to the wall of the vehicle prior to positioning the insulation layer over the wall of the vehicle.

20. The method of claim 13, wherein the test cage is a first test cage and further comprising positioning a second test cage in the gap and away from the first test cage and testing air pressure of the gap at the second test cage.

* * * * *